United States Patent
Saebo et al.

(10) Patent No.: US 6,410,761 B1
(45) Date of Patent: Jun. 25, 2002

(54) CONJUGATED LINOLEIC ACID COMPOSITIONS AND METHODS OF MAKING SAME

(75) Inventors: Asgeir Saebo, Oersta (NO); Carl Skarie, Detroit Lakes; Daria Jerome, Owatonna, both of MN (US); Gudmunder Haroldsson, Reykjavik (IS)

(73) Assignee: Conlinco, Inc., Detroit Lakes, MN (US)

( * ) Notice: Subject to any disclaimer, the term of this patent is extended or adjusted under 35 U.S.C. 154(b) by 0 days.

(21) Appl. No.: 09/270,940

(22) Filed: Mar. 17, 1999

Related U.S. Application Data

(63) Continuation-in-part of application No. 09/132,593, filed on Aug. 11, 1998, which is a continuation-in-part of application No. 09/160,416, filed on Sep. 25, 1998, which is a continuation-in-part of application No. 09/042,538, filed on Mar. 17, 1998, now abandoned, which is a continuation-in-part of application No. 09/042,767, filed on Mar. 17, 1998, now Pat. No. 6,015,833.

(51) Int. Cl.$^7$ ................................................ C11C 3/00
(52) U.S. Cl. .................... 554/126; 554/167; 554/168; 554/173
(58) Field of Search .................. 554/126, 156, 554/157, 173

(56) References Cited

U.S. PATENT DOCUMENTS 5,468,887 A  * 11/1995 Gupta et al. ................ 554/169

FOREIGN PATENT DOCUMENTS

AU           253031       *  5/1961  ................. 554/126

OTHER PUBLICATIONS

Suzuki et al, Method for manufacturing 1,2–saturated–3–unsaturated trigylcerides using lipase, JP 10025491, citation and abs, Jan. 27, 1998.*
Hashizume et al Manufacture of higly–unsaturated fatty acids with Lipase, JP 02025447 citation and abs, 1990.*
Klemann, Acid–hydrolyzable ester derivatives as low calorie fat mimetics, US 5068119, citation, 1991.*
Arcos et al, Rapid enzymatic production of acylglycerols from conjugated linoleic acid and glycerol in a solvent–free system; Biotechnology Letters, vol. 20 No., pp. 617–621, Jun. 1998.*

* cited by examiner

*Primary Examiner*—Deborah D. Carr
(74) *Attorney, Agent, or Firm*—Medlen & Carroll, LLP

(57) ABSTRACT

Novel compositions containing conjugated linoleic acids are efficacious as animal feed additives and human dietary supplements. Linoleic acid is converted to its conjugated forms in which the resulting composition is low in certain unusual isomers compared to conventional conjugated linoleic products.

6 Claims, 1 Drawing Sheet

CONJUGATED LINOLEIC ACID COMPOSITIONS AND METHODS OF MAKING SAME

RELATED APPLICATIONS

This application is continuation-in-part of U.S. Ser. No. 09/132,593, filed Aug. 11, 1998, and U.S. Ser. No. 09/160,416, filed Sep. 25, 1998, which is a continuation-in-part of U.S. Ser. No. 09/042,538, filed Mar. 17, 1998, now abandoned and U.S. Ser. No. 09/042,767, filed Mar. 17, 1998, now U.S. Pat. No. 6,015,833 incorporated herein by reference.

FIELD OF THE INVENTION

The present invention relates to the field of human and animal nutrition, and in particular to certain novel compositions of conjugated linoleic acids (CLA). These compositions are prepared according to a novel method that controls isomerization of 9,12-linoleic acid.

BACKGROUND OF THE INVENTION

In 1978, researchers at the University of Wisconsin discovered the identity of a substance contained in cooked beef that appeared to inhibit mutagenesis. The substance was found to be a mixture of positional isomers of linoleic acid (C18:2) having conjugated double bonds. The c9,t11 and t10,c12 isomers are present in greatest abundance, but it is uncertain which isomers are responsible for the biological activity observed. It has been noted from labelled uptake studies that the 9,11 isomer appears to be somewhat preferentially taken up and incorporated into the phospholipid fraction of animal tissues, and to a lesser extent the 10,12 isomer. (See Ha, et al., Cancer Res., 50: 1097 (1991)).

The biological activity associated with conjugated linoleic acids (termed CLA) is diverse and complex. At present, very little is known about the mechanisms of action, although several preclinical and clinical studies in progress are likely to shed new light on the physiological and biochemical modes of action. The anticarcinogenic properties of CLA have been well documented. Administration of CLA inhibits rat mammary tumorigenesis, as demonstrated by HA, et al., Cancer Res., 52: 2035s (1992). Ha, et al., Cancer Res., 50: 1097 (1990) reported similar results in a mouse forestomach neoplasia model. CLA has also been identified as a strong cytotoxic agent against target human melanoma, colorectal and breast cancer cells in vitro. A recent major review article confirms the conclusions drawn from individual studies (Ip, Am. J. Clin. Nutr., 66 (6 Supp): 1523s (1997)).

Although the mechanisms of CLA action are still obscure, there is evidence that some component(s) of the immune system may be involved, at least in vivo. U.S. Pat. No. 5,585,400 (Cook, el al.), incorporated herein by reference, discloses a method for attenuating allergic reactions in animals mediated by type I or TgE hypersensitivity by administering a diet containing CLA. CLA in concentrations of about 0.1 to 1.0 percent was also shown to be an effective adjuvant in preserving white blood cells. U.S. Pat. No. 5,674,901 (Cook, et al.), incorporated herein by reference, disclosed that oral or parenteral administration of CLA in either free acid or salt form resulted in elevation in CD-4 and CD-8 lymphocyte subpopulations associated with cell-mediated immunity. Adverse effects arising from pretreatment with exogenous tumor necrosis factor could be alleviated indirectly by elevation or maintenance of levels of CD-4 and CD-8 cells in animals to which CLA was administered. Finally, U.S. Pat. No. 5,430,066, incorporated herein by reference, describes the effect of CLA in preventing weight loss and anorexia by immune stimulation.

Apart from potential therapeutic and pharmacologic applications of CLA as set forth above, there has been much excitement regarding the use of CLA nutritively as a dietary supplement. CLA has been found to exert a profound generalized effect on body composition, in particular redirecting the partitioning of fat and lean tissue mass. U.S. Patent No. 5,554,646 (Cook, et al.), incorporated herein by reference, discloses a method utilizing CLA as a dietary supplement in which pigs, mice, and humans were fed diets containing 0.5 percent CLA. In each species, a significant drop in fat content was observed with a concomitant increase in protein mass. It is interesting that in these animals, increasing the fatty acid content of the diet by addition of CLA resulted in no increase in body weight, but was associated with a redistribution of fat and lean within the body. Another dietary phenomenon of interest is the effect of CLA supplementation on feed conversion. U.S. Pat. No. 5,428,072 (Cook, et al.), incorporated herein by reference, provided data showing that incorporation of CLA into animal feed (birds and mammals) increased the efficiency of feed conversion leading to greater weight gain in the CLA supplemented animals. The potential beneficial effects of CLA supplementation for food animal growers is apparent.

Another important source of interest in CLA, and one which underscores its early commercial potential, is that it is naturally occurring in foods and feeds consumed by humans and animals alike. In particular, CLA is abundant in products from ruminants. For example, several studies have been conducted in which CLA has been surveyed in various dairy products. Aneja, el al., J. Dairy Sci., 43: 231 (1990) observed that processing of milk into yogurt resulted in a concentration of CLA. (Shanta, et al., Food Chem., 47: 257 (1993)) showed that a combined increase in processing temperature and addition of whey increased CLA concentration during preparation of processed cheese. In a separate study, Shanta, et al., J. Food Sci., 60: 695 (1995) reported that while processing and storage conditions did not appreciably reduce CLA concentrations, they did not observe any increases. In fact, several studies have indicated that seasonal or interanimal variation can account for as much as three fold differences in CLA content of cows milk. (e.g., see Parodi, et al., J. Dairy Sci., 60: 1550 (1977)). Also, dietary factors have been implicated in CLA content variation, as noted by Chin, et al., J. Food Camp. Anal., 5: 185 (1992). Because of this variation in CLA content in natural sources, ingestion of prescribed amounts of various foods will not guarantee that the individual or animal will receive the optimum doses to ensure achieving the desired nutritive effect.

Linoleic acid is an important component of biolipids, and comprises a significant proportion of triglycerides and phospholipids. Linoleic acid is known as an "essential" fatty acid, meaning that the animal must obtain it from exogenous dietary sources since it cannot be autosynthesized. Incorporation of the CLA form of linoleic acid may result in a direct substitution of CLA into lipid positions where unconjugated linoleic would have migrated. But this has not been proven, and some of the highly beneficial but unexplained effects observed may even result from a repositioning of CLA within the lipid architecture at sites where unconjugated linoleic acid would not have otherwise migrated. It is now clear that one source of animal CLA, especially in dairy products, comes from the biochemical action of certain rumen bacteria on native linoleic acid, first isomerizing the linoleic acid to CLA, and then secreting it into the rumen cavity. Kepler, et al., *J. Nutrition*, 56: 1191 (1966) isolated a rumen bacterium, *Butyrivibrio fibrisolvens*, which catalyzes formation of 9,11-CLA as an intermediate in the biohydrogenation of linoleic acid. Chin, et al., *J. Nutrition*, 124: 694 (1994) further found that CLA found in the tissues of rodent was associated with bacteria, since corresponding germ-free rats produced no CLA.

In the development of a defined commercial source of CLA for both therapeutic and nutritional application, a process for generating large amounts of defined material is needed. The problem with most CLA products made by conventional approaches is their heterogeneity, and substantial variation in isoform from batch to batch. Considerable attention has been given to the fact that the ingestion of large amounts of hydrogenated oils and shortenings, instead of animal tallow, has resulted in a diet high in trans-fatty acid content. For example, Holman, et al., *PNAS*, 88:4830 (1991) showed that rats fed hydrogenated oils gave rise to an accumulation in rat liver of unusual polyunsaturated fatty acid isomers, which appeared to interfere with the normal metabolism of naturally occurring polyunsaturated fatty acids. These concerns were summarized in an early Editorial in *Am. J. Public Health*, 84: 722 (1974). Therefore, there exists a strong need for a biologically active CLA product of defined composition.

SUMMARY OF THE INVENTION

The present invention provides a novel compositions of isomerized fatty acids derived from clarified food grade seed oils. The linoleic acid contained in a seed oil selected as having at least 50 percent linoleic acid, as a practical matter, is typically in excess of 90 percent the 9,12-octadecadienoic isomer. During isomerization, the 9,12-octadecadienoic acid is converted to a mixture of other isomers to form a composition having at least 50 percent CLA.

The conjugated linoleic acid-containing composition is intended for consumption by both humans and animals, including food animals such as cattle, swine, sheep, and birds, and as a human medicament and a nutritional supplement. It is an important object of this invention to provide a safe, defined product for these applications. Also, conventional products contain significant quantities of unknown fatty acid species and unusual isomers resulting from processing. Among the unusual CLA isomers are the 11,13-octadecadienoic acid and 8,10-octadecadienoic acid isomers.

In the present composition, a high percentage of linoleic acid is converted primarily to the conjugated c9,t11 and t10,c12 isomers in a carefully controlled reaction yielding greater than 90 percent of these isomers, so that less than a combined 1 percent of the 11,13 isomers, less than 1 percent of the 8,10 isomers, less than 1 percent of the double trans species (the t9,t11 and t10,t12 isomers), and less than 1 percent total unidentified linoleic acid species is present in contrast to conventional compositions. In many individual product runs, the final composition has levels of these species virtually undetectable by GC analysis. The 1 percent limit in concentration of the 11,13, 8,10 and trans-trans isomers serves as a convenient and practical quality assurance standard of purity for a commercial scale manufactured food grade product.

The present invention also provides a new process for making novel conjugated linoleic acid-containing compositions of the requisite purity and defined composition. The process comprises the steps of dissolving in the specific non-aqueous solvent propylene glycol, an alkali compatible with a non-aqueous medium such as potassium hydroxide, cesium hydroxide, cesium carbonate, or an organic alkali such as tetraethyl ammonium hydroxide, in the absence of metallic-based isomerization catalyst systems, blending into the alkaline propylene glycol a seed oil, heating under an inert gas atmosphere and at ambient pressures to a temperature in the range of 130–165 degrees C., preferably about 150 degrees C. under non-reflux conditions, separating the fatty acid fraction by acidification, and optionally further purifying and dehydrating by vacuum molecular distillation and/or centrifugation. Optionally, the process stream may be interrupted after the reaction mix is prepared, either prior to or after the heat step. The mix may then be stored for further processing in continuous acidification and distillation steps and/or be further processed at another location. After heating to effect isomerization, the isomerized blended reaction mix contains 30–60 percent processed seed oil, 10–40 percent alkali, and 30–60 percent propylene glycol. In this process it is important to utilize propylene glycol because of its heating properties and the patterns of isomerization obtained. The components of the dissolved fatty acid reaction mix are present, as follows:

30–60 percent seed oil
10–40 percent alkali
30–60 percent propylene glycol

Thus, in some embodiments, the process comprises forming a blended reaction mix containing linoleic acid-containing seed oil, propylene glycol, and an alkali compatible with a nonaqueous medium, isomerizing said linoleic acid contained in said seed oil by heating to form conjugated linoleic acids, aquefying to release glycerol. Toxicity is avoided, as will be posed if other, undesirable organic solvents such as ethylene glycol are used. Under the non-reflux conditions, it is possible to vary the processing temperature over a range to obtain the desired result with oils of differing fatty acid composition. The temperature is critical, as the percentage of trans,trans species, as well as other undesired and unidentified species increases as temperature rises. The processing time requires about 2 to 6.5 hours and gives isomerized yields of greater than 90 percent, frequently as high as 99.5 percent. In some embodiments, the linoleic acid containing seed oil may first be treated to produce alkylesters (e.g. methylesters or ethylesters) of the linoleic acid. In still other embodiments, the conjugated linoleic acids produced can be incorporated into a triglyceride by treating with a lipase in the presence of glycerol. In other embodiments, the present invention provides the low impurity CLA preparation produced by the above processes.

In the present process, use of sunflower and safflower oil is preferred because of its high native 9,12 linoleic acid content, but also because of low levels of sterols, contaminating phospholipids, and other residues that tend to foul the processing equipment and result in a less pure final product. Other seed oils, such as corn, soybean, and linseed oils, may also be employed, but the final product will be less compositionally defined, and. the impurity levels may stray to close to the threshold values for quality control contemplated above, and the isomerization process itself will be less predictable. While a seed oil containing at least 50 percent linoleic acid is desirable as a practical matter for industrial isomerization, so as to optimize yields per processing unit, there is no process limitation in starting with linoleic acid-containing materials having less or greater linoleic content. Lesser linoleic content may occur as in the situation in which oils from different sources are blended, or where oils are combined with non-oil components prior to isomerization. Similarly, the linoleic acid content of the isomerization fluid can be much higher than the levels present in native seed oils, as in the situation in which purified or synthetic linoleic is to be isomerized.

In some embodiments, the low impurity CLA described above may be provided as acylglycerols or alkylesters. Accordingly, in some embodiments, an acylglycerol composition is provided which comprises a plurality of acylglycerol molecules of the structure:

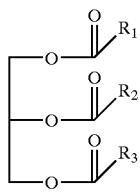

wherein $R_1$, $R_2$, and $R_3$ are selected from the group consisting of a hydroxyl group and an octadecadienoic acid, the composition characterized in containing at least approximately 30% t10,c12 octadecadienoic acid, at least approximately 30% c9,t11 octadecadienoic acid, and about less than 1% total of 8,10 octadecadienoic acid, 11,13 octadecadienoic and trans-trans octadecadienoic acid at positions $R_1$, $R_2$, and $R_3$. Likewise, in other embodiments, a conjugated linoleic acid composition comprising a mixture of esters of conjugated linoleic acid isomers is provided, the mixture containing at least approximately 30% t10,c12 octadecadienoic acid, at least approximately 30% c9,t11 octadecadienoic acid, and about less than 1% total of 8,10 octadecadienoic acid, 11,13 octadecadienoic and trans-trans octadecadienoic acid.

In alternative embodiments, the CLA free fatty acids, acylglycerols and alkylesters of the present invention may be formulated with food products, including animal feeds and food for human consumption. In other embodiments, the CLA compositions of the present invention may be formulated with physiologically acceptable carriers or oral delivery vehicles. In other embodiments, the biological effects of the low impurity CLA may be utilized.

In the present invention, a feed or food safe conjugated linoleic acid alkyl ester is manufactured under conditions preferentially controlling isomerization to the desired 10,12 and 9,11 isomers, while limiting formation of 8,10; 11,13; and trans,trans species. Such conditions are met by employing an alkali alcoholate catalyzed reaction in which a seed oil is split to release free fatty acids from a glycerol backbone and then esterifying prior to isomerization. The key to an adaptation of this process to a commercially viable product is reduction in the process steps which add cost. Typically, residues derived from non-oil components of seed oils, such as sterols and phosphatides, foul equipment and reduce palatability for feed or food use. In the case of typical seed oils such as soy or corn these residues are present in sufficient quantity that a CLA-ester product could not be used in consumable products.

In the composition of the present invention, non-oil residues are not purified away from the oil component, but rather the source of oil is selected to maintain such residues at acceptable levels. By selecting safflower or sunflower oil as an oil source, critical residue levels can be controlled to between 0.1 and 0.5% phosphatides, and to an unsaponifiable sterol fraction containing between 5 and less than 20 percent each of campesterol and stigmasterol, without extensive degumming and distillation processing steps. The resulting linoleic acid alkyl ester is comprised of at least 50 percent up to about 99 percent by weight of octadecanoic acid ester isomers representing combinations of various possible individual percentages of c9,t11-octadecanoic acid alkyl ester and t10,c12-octadecanoic acid alkyl ester. In the alkali alcoholate catalyzed process roughly equal amounts of each of these ester isomers are produced, but the relative percentages can by altered by addition of one or the other of a composition enriched for one isomer. The CLA ester may then be incorporated into an animal feed by compounding the feed from conventional ingredients in a ration typical for the species and age of the animal, and blending therewith the conjugated linoleic acid alkyl esters in a biologically active concentration, generally about 0.05 to 3.5 percent by weight.

The CLA-ester product of the present invention is obtained by direct isomerization of an unrefined linoleic acid, e.g. a linoleic acid source not subjected to refining steps. The CLA-ester composition has one part comprising at least 50 percent by weight of ester isomers (up to substantially 100 percent) of a mixture of ester isomers of c9,t11-octadecanoic acid ester and t10,c12 -octadecanoic acid ester, a second part comprising less than about 5% percent, preferably less than about 1%, by aggregate weight of ester isomers of the structure 8,10-octadecanoic acid ester, 11,13-octadecanoic acid ester, and trans,trans-octadecanoic acid esters, and a third part containing a phosphatidyl residue of between 0.1 and 0.5 percent of the total composition weight. The alkyl groups may be methyl, ethyl, propyl, isopropyl, butyl, isobutyl and the like. Adjustments in concentration of the c9,t11 and t10,c12 isomers can be made by addition of a composition enriched for one or the other isomer to yield an ester composition wherein the c9,t11, or the t10,c12 respectively contained in the first composition part constitutes greater than 60 percent of the total isomers of octadecanoic acid esters.

In the process embodiment of the present invention resulting in a food grade composition suitable for an animal feed, food ingredient, or human dietary supplement, an unrefined CLA-ester having a phosphatidyl residue less than 0.5 percent is treated with an alkali alcoholate in the presence of a monohydric low molecular weight alcohol such as methyl or ethyl alcohol, continuing the treatment at low temperature (about 90 to 145 degrees C.) until at least 50 percent of the ester is converted to CLA-ester, acidifying by addition of an aqueous acid, and then separating the CLA-ester from the aqueous acid without a distillation step.

DETAILED DESCRIPTION OF THE INVENTION

Definitions

Figure 1:
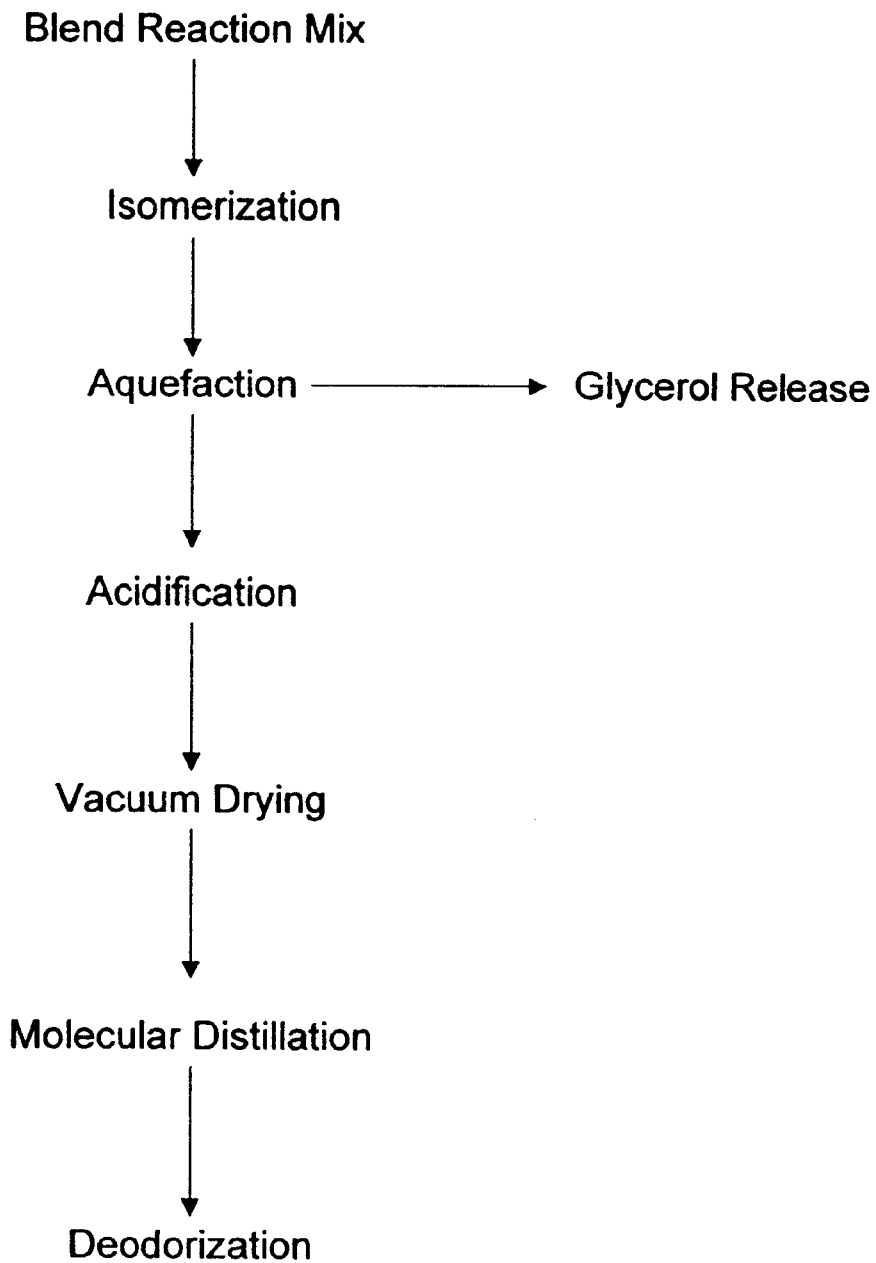
FIG. 1 is a flow diagram of the procedure used to produce CLA.

As used herein, "conjugated linoleic acid" or "CLA" refers to any conjugated linoleic acid or octadecadienoic free fatty acid. It is intended that this term encompass and indicate all positional and geometric isomers of linoleic acid with two conjugated carbon-carbon double bonds any place in the molecule. CLA differs from ordinary linoleic acid in that ordinary linoleic acid has double bonds at carbon atoms 9 and 12. Examples of CLA include cis- and trans isomers ("E/Z isomers") of the following positional isomers: 2,4-octadecadienoic acid, 4,6-octadecadienoic acid, 6,8-octadecadienoic acid, 7,9-octadecadienoic acid, 8,10-octadecadienoic acid, 9,11-octadecadienoic acid and 10,12 octadecadienoic acid, 11,13 octadecadienoic acid. As used herein, "CLA" encompasses a single isomer, a selected mixture of two or more isomers, and a non-selected mixture of isomers obtained from natural sources, as well as synthetic and semisynthetic CLA.

As used herein, it is intended that "triglycerides" of CLA contain CLA at any or all of three positions on the triglyceride backbone. Accordingly, a triglyceride containing CLA may contain any of the positional and geometric isomers of CLA.

As used herein, it is intended that "esters" of CLA include any and all positional and geometric isomers of CLA bound through an ester linkage to an alcohol or any other chemical group, including, but not limited to physiologically acceptable, naturally occurring alcohols (e.g., methanol, ethanol, propanol). Therefore, an ester of CLA or esterified CLA may contain any of the positional and geometric isomers of CLA.

It is intended that "non-naturally occurring isomers" of CLA include, but are not limited to c11,t13; t11,c13; t11,t13; c11,c13; c8,t10; t8,c10; t8,t10; c8,c10; and trans-trans isomers of octadecadienoic acid, and does not include t10,c12 and c9,t11 isomers of octadecadienoic acid. "Non-naturally occurring isomers" may also be referred to as "minor isomers" of CLA as these isomers are generally produced in low amounts when CLA is synthesized by alkali isomerization.

As used herein, "low impurity" CLA refers to CLA compositions, including free fatty acids, alkylesters, and triglycerides, which contain less than 1% total 8,10 octadecadienoic acids, 11,13 octadecadienoic acids, and trans-trans octadecadienoic acids.

"Prepared food product" means any pre-packaged food approved for human consumption.

As used herein, "c" encompasses a chemical bond in the cis orientation, and "t" refers to a chemical bond in the trans orientation. If a positional isomer of CLA is designated without a "c" or a "t", then that designation includes all four possible isomers. For example, 10,12 octadecadienoic acid encompasses c10,t12; t10,c12; t10,t12; and c10,c12 octadecadienoic acid, while t10,c12 octadecadienoic acid or CLA refers to just the single isomer.

As used herein, the term "oil" refers to a free flowing liquid containing long chain fatty acids (e.g., CLA) or other long chain hydrocarbon groups. The long chain fatty acids, include, but are not limited to the various isomers of CLA.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed).

The composition of the present invention results from a highly controlled isomerization process, and from using the preferred starting material of sunflower or safflower oil. This composition has not heretofore been obtained, for application to an industrial scale, because the conventional processes historically produce conjugated linoleic acids for entirely different purposes, namely, as drying oils in the paint industry. Also, there has not been an appreciation of the implications of the isomer content of the final product, because the analytical methods for characterizing the fatty acids has not been widely available.

In the older isomerization processes, some of which are still in use in more modern format, production of the conjugated fatty acids was carried out in aqueous alkali (generally NaOH) at high temperatures in excess of 200 degrees C. and usually at superatmospheric pressures. For example, U.S. Pat. No. 2,350,583 (Bradley) discloses an aqueous alkali process utilizing treated soaps in which both conjugation and polymerization occurred under rather harsh conditions at 200 to 250 degrees C. for a period of several hours. The fractions of drying oil, starting with linseed oil, were obtained by distillation (see also Br. Pat. No. 558,881 for a very similar process). In a variation of the process, U.S. Pat. No. 4,381,264 teaches a process where a low water content reaction zone (0.5% water) contains stoichiometric base in the presence of $SO_2$ to obtain conjugation of the double bonds of various polyunsaturated fatty acids. The aqueous alkali process was adapted in U.S. Pat. No. 4,164,505 to a continuous flow process in which an alkali metal hydroxide and water are continuously charged in a flow zone maintained at between 200 and 370 degrees C. At these temperatures, the time of reaction should be greatly foreshortened, but there is relatively little control over the isomerization. At the higher end of the temperature range, one would predict almost complete conversion to double trans species.

Methods of producing CLA using various nonaqueous solvents and catalysts have been described in the literature. Burr (U.S. Pat. No. 2,242,230) discloses the use of solvents such as methanol, butanol, ethanol and glycol in combination with various catalysts. These reaction parameters are summarized in Table 1. With the exception of glycol, the reactions were conducted either under reflux conditions or in sealed tubes. These reaction conditions result in imprecise control of two of the important reactions parameters identified by the Inventors- temperature and pressure. Imprecise control of these reactions parameters is likely to lead to less than complete conjugation and the formation of undesirable isomers.

TABLE 1

| U.S. Pat. No. 2,242,230 | | | |
|---|---|---|---|
| Solvent | Catalyst | Temperature | Time |
| Ethanol | KOH, NaOH | reflux or higher* | varied |
| Butanol | KOH, NaOH | reflux or higher* | varied |
| Glycol | KOH | 195° C. | varied |
| Isoamyl Alcohol | KOH | reflux or higher* | varied |
| Butanol | Tributyl-amine | 140–175° C. | 22 hours |
| Butanol | Potassium Acetate | 175° C. | 36 hours |
| Butanol | Trisodium Phosphate | 175° C. | 36 hours |
| Butanol | Potassium Phosphate | 175° C. | 36 hours |
| Butanol | Sodium Benzoate | 175° C. | 36 hours |
| Butanol | Potassium Thiocyanate | 175° C. | 36 hours |
| Butanol | Borax | 175° C. | 36 hours |

Likewise, Baltes el al., (U.S. Pat. No. 3,162,658) disclose the use of nonaqueous solvents and various metallic bases as catalysts for the conjugation of fatty acids. The various reaction parameters of the methods described by Baltes et al. are summarized in Table 2. Baltes et al. also disclose the use various low boiling point solvents. As most of these reactions were conducted at temperatures above the boiling point of the solvent employed, it is apparent that the reactions were conducted under pressure, which is an independent factor influencing the formation of octadecadienoic acid isomers. The product derived from these reactions will thus contain undesirable isomers.

TABLE 2

U.S. Pat. No. 3,162,658

| Solvent | Catalyst | Temperature | Time |
|---|---|---|---|
| Methanol | KOH | 60–140° C. | variable |
| Methanol | Potassium Methylate | 140° C. | variable |
| Butanol | Potassium Methylate | 140° C. | variable |
| Ethanol | Potassium Methylate | 140° C. | variable |
| Isopropanol | Potassium Methylate | 120–140° C. | variable |
| Heptane/ 3° Butanol | Potassium Butylate | reflux | variable |
| 3° Butanol | Cesium Butylate | 140° C. | variable |
| Ethylene Diamine | Potassium Methylate | 140–160° C. | variable |
| Methanol | Sodium Amide | 140° C. | variable |

The CLA of the present invention lacks isomers such as the 8,10 isomer, the 11,13 isomer, and the various trans-trans isomers. This composition was produced by a tightly controlled nonaqueous alkali isomerization process presented in flow diagram form in FIG. 1. Preferably, sunflower oil or safflower oil are reacted at an ambient pressure under an inert gas atmosphere with an excess of alkali in a high-boiling point solvent, namely propylene glycol at a temperature below the boiling point of the solvent. These reaction conditions allow for precise control of the temperature (and constant ambient pressure) of the conjugation process. Preferably the alkali is an inorganic alkali such as potassium hydroxide, cesium hydroxide, cesium carbonate or an organic alkali such as tetraethyl ammonium hydroxide. The catalyst is preferably provided in a molar excess as compared to the fatty acid content of oil. The solvent is propylene glycol. Preferably, the reaction is conducted within a temperature range 130 to 165° C., most preferably at about 150° C. The time of the reaction may vary, however, there is an increased likelihood of the formation of undesirable isomers when the reaction is conducted for long periods of time. A relatively short reaction time of 2.0 to 6.5 hours has proved satisfactory for excellent yields.

It will be understood to a person skilled in the art that to produce the desired composition, the reaction conditions described above may be varied depending upon the oil to be conjugated, the source of alkali and equipment. Preanalysis of a particular oil may indicate that the conditions must be varied to obtain the desired composition. Therefore, the temperature range, pressure, and other reaction parameters represent a starting point for design of the individual process and are intended as a guide only. For example, it is not implied that the described temperature range is the only range which may be used. The essential aspect is to provide precise temperature control. However, care must be taken because increasing the pressure may lead to less than complete isomerization and the formation of undesirable isomers. Finally, the length of the conjugation reaction may be varied. Generally, increasing amounts of undesirable isomers are formed with increasing length or reaction. Therefore, the optimal reaction time allows the reaction to go nearly or essentially to completion but does not result in the formation of undesirable isomers.

Following the conjugation reaction, the resulting CLA containing composition may be further purified according to FIG. 1. To separate the fatty acids form the conjugation reaction mix, the reaction mix is cooled to approximately 95° C., an excess of water at 50° C. is added, and the mixture slowly stirred while the temperature is reduced to about 50° C. to 60° C. Upon addition of the water, a soap of the fatty acids is formed and glycerol is formed as a by-product. Next, a molar excess of concentrated HCl is added while stirring. The aqueous and nonaqueous layers are then allowed to separate at about 80–90° C. The bottom layer containing water and propylene glycol is then drawn off. The remaining propylene glycol is removed by vacuum dehydration at 60–80° C.

The dried CLA composition may then preferably be degassed in degassing unit with a cold trap to remove any residual propylene glycol. Next, the CLA is distilled at 190° C. in a molecular distillation plant at a vacuum of $10^{-1}$ to $10^{-2}$ millibar. The advantage of this purfication system is the short time (less than one minute) at which the CLA is held at an elevated temperature. Conventional batch distillation procedures are to be strictly avoided since they involve an elevated temperature of approximately 180–200° C. for up to several hours. At these elevated temperatures the formation of undesirable trans-trans isomers will occur. Approximately 90% of the feed material is recovered as a slightly yellow distillate. The CLA may then be deodorized by heating to about 120–170° C., preferably at about 150° C. for 2 hours to improve smell and taste. Excessive heat may result in the formation of trans-trans isomers. These procedures produce a CLA composition with a solvent level of less than about 5 ppm, preferably less than about 1 ppm. This process eliminates toxic trace levels of solvent so that the resulting composition is essentially free of toxic solvent residues.

The processes described above are readily adaptable to both pilot and commercial scales. For example, 400 kg of safflower oil may be conjugated at 150° C. for 5 hours in 400 kg of propylene glycol with 200 kg KOH added as a catalyst. The resulting CLA may then be purified as described above. Further, commercial scale batch systems may be easily modified to produce the desired CLA composition. For example, stainless steel reactors should be preferably glass lined to prevent corrosion due to pH levels of below 3.0. However, it should be noted that conjugation processes utilizing nonaqueous solvents are generally less corrosive than those conducted with water.

The preferred oils for conjugation are sunflower and safflower oil. As compared to soybean oil, these oils have lower concentrations of undesirable components such as phosphatides and sterols. These undesirable components may contribute to the formation of gums which foul the conjugation equipment and other undesirable polymers. Various properties of these oils are summarized in Tables 3, 4, and 5.

TABLE 3

Phosphatides

| | |
|---|---|
| Soybean | 1.5–3.0% |
| Sunflower | .4–1% |
| Sunflower | .4–1% |

TABLE 4

Sterols (unsaponifiables by percent*)

| Soybean | | Sunflower | | Safflower | |
|---|---|---|---|---|---|
| Campesterol | 20* | Campesterol | 8 | Campesterol | 13 |
| Stigmasterol | 20 | Stigmasterol | 8 | Stigmasterol | 9 |
| β-Sitosterol | 53 | β-Sitosterol | 60 | β-Sitosterol | 52 |
| $\Delta^5$ Avensterol | 3 | $\Delta^5$ Avensterol | 4 | $\Delta^5$ Avensterol | 1 |
| $\Delta^7$ Stigmasterol | 3 | $\Delta^7$ Stigmasterol | 15 | $\Delta^7$ Stigmasterol | 15 |
| $\Delta^7$ Avensterol | 1 | Avenasterol | 4 | Avenasterol | 3 |
| 0.36% total in oil | | 0.36% total in oil | | 0.36% total in oil | |

*May not equal 100

TABLE 5

| | Soybean | Sunflower | Safflower |
|---|---|---|---|
| Iodine Value | 134.6 | 135.4 | 143.6 |
| Saponification value | 190.7 | 190.6 | 190.3 |
| Unsaponification value | .6 | .7 | .6 |

In the Examples that follow, several comparative experiments were carried out to highlight the key properties of the present CLA compositions in contrast to those made under either suboptimal conditions or in accordance with the aqueous alkali methods of the prior art. In Example 1, the CLA was prepared by the present method. CLA was produced by the conventional aqueous alkali method in Example 2. In Example 3, the reaction of Example 1 is substantially repeated, only at high temperature. Finally, in Example 4, the aqueous alkali reaction substantially identical to that of Example 2 is run at low temperature. The precise conditions and details of each experiments are set forth in the Examples. The profiles of the analysis of the CLA isomer content are set forth in tables 1–4.

Referring to the data in Table 10, the relative area percentage is given for each identified peak corresponding to the individual isomers, for each of the four experiments. The GC plot gave a number of peaks for each sample tested. The area under each of these peaks was integrated to obtain a total value. The identity of the peak was determined by its relative position, from published atlases of standard elution profiles, and the scientific literature. The top row represents the residual value for unconjugated starting material, 9,12-linoleic acid. Both low and high temperature reaction in propylene glycol gave extremely high conversions of over 99 percent of the total starting material.

Referring to column 1, it is strikingly apparent that unlike any of the control compositions, in Example 1, a peak corresponding to 11,13 mixture of isomers, the peak corresponding to c11,c13 specifically, the peaks for any of the 8,10 isomers, and the peak for unidentified isomers are all entirely missing. In the case of c9,t11 isomer, the peaks in GC for both the 8,10 and 9,11 isomers are superimposed, and are here resolved only for Example 1 material by subtracting out that portion of the peak identified as 8,10 by NMR studies. This was not done in the other experiments, so that row 3 gives the values for combined 8,10 and 9,11 for Examples 2–4. In general, for the 8,10, 11,13, and unidentified isomers, a value of less than 1 percent down to undetectable is of therapeutic and nutritional value, because it reduces to trace levels potentially deleterious contaminants, especially those known to have suspect absorption pathways in lipogenesis. In non-ruminants, for example, addition of 0.25 to 2.5 percent CLA to the diet can increase the incidence of CLA in tissues to approximate that in ruminants, so that other animals can be a source of CLA provided adulterating isomers are not present.

Example 2 provides a typical aqueous alkali product representative of conventionally manufactured CLAs. Conversion is less efficient both overall, and in producing the c9,t11 and t10,c12 isomers. Note also a high percentage of the suspect 11,13 isomers, and a significant percentage of unidentified material.

Example 3 illustrates the criticality of the temperature parameter. An upward shift in temperature in propylene glycol media sharply increases the amount of the contaminating isomers at the expense of the c9,t11 and t10,c12 isomers. Also of interest, at the higher temperature there is a dramatic increase in the trans, trans species, as double bond rearrangements are favored which yield a more stable electron configuration at levels of increased energy stress.

Example 4 illustrates that decreasing the temperature in the aqueous alkali system, in fact, reduces the amounts of some of the contaminating isomers. However, there is a dramatic drop in yield, and the level of the 11,13 group of isomers remains very high, suggesting that the formation of this electron configuration is influenced more by the action of base in an aqueous medium, than is explained by overall kinetic energy in the system. Note also the extremely long reaction time of 22.5 hours; too long for an efficient industrial scale batch process.

Table 11 merely converts the relative isomer percentages in the various reactions as a function of peak area to their corresponding peak ratios. The present process produces a virtually complete conversion of 9,12-linoleic acid to an approximate equal amount of each of the two desired CLA isomers. At the higher temperature, even in propylene glycol, the incidence of the 11,13 isomer is still less one third that of the low temperature aqueous alkali process.

In some embodiments, the present invention also provides methods for producing alkyl esters of CLA. After fat splitting and dehydration, the free fatty acids are combined with methanol or other monohydric low molecular weight alcohol and heated to the temperature at which the alcohol boils. Esterification proceeds under refluxing conditions with removal of the reaction water through a condenser. After the addition of a further quantity of the same or a different monohydric alcohol an alcoholate catalyst is blended into the ester mix. Typical alcoholate catalysts are sodium or potassium ethoxide, or their methyl, butyl, or propyl counterparts.

In the esterification, methanol or ethanol are preferred, although other branched or straight chain monohydric alcohols may be used. The longer the aliphatic chain of the alkyl group, the more lipid compatible the material becomes. Also the viscosity tends to increase. For different types of feed or food, whose consistency varies, product of varying viscosity can be used to obtain the desired flow or compounding characteristics without affecting the therapeutic or nutritional properties arising from the CLA moieties. The theory and practice of esterification are conventional. A basic explanation of the most common methods is set forth in the McCraw-Hill Encyclopedia of Science & Technology, McGraw-Hill Book Co., N.Y.: 1996 (5th ed.). The animal and human body has a variety of esterases, so that the CLA-ester is cleaved to release the free fatty acids readily. Tissue uptake may have a different kinetics depending on the tissue involved and the benefit sought.

In the isomerization step, it was found that alcoholate catalysis produced a much superior product than aqueous alkali mediated isomerization. The latter process always produced undesirable isomers even under mild reaction conditions. The milder conditions do give lower amounts of unwanted isomers, but at the great expense of yield, as shown in the Examples. In most systems the appearance of the c9,t11 and t10,c12 isomers dominates and they are formed in roughly equimolar amounts. It has not heretofore been possible to control the isomerization of the one isomer to the exclusion of the other. While it is desirable to increase the percentage of one or the other isomer (depending on the physiological effect to be achieved), at present this must largely be carried out by adding an enriched source of the desired isomer.

The present invention contemplates the use of derivatives of the pure preparation of CLA. For example, CLA may be free or bound through ester linkages or provided in the form of an oil containing CLA triglycerides, as described in Examples 5 and 6. In these embodiments, the triglycerides may be partially or wholly comprised of CLA attached to a glycerol backbone. The CLA may also preferably be provided as a methylester or ethylester as described in Examples 8 and 9. Furthermore, the CLA may be in the form of a non-toxic salt, such as a potassium or sodium salt (e.g., a salt formed by reacting chemically equivalent amounts of the free acids with an alkali hydroxide at a pH of about 8 to 9).

In one embodiment of the present invention, a novel triacylglycerol is synthesized comprising the novel CLA isomer mixture disclosed hereinafter for non-aqueous isomerization of linoleic acid from sunflower and/or safflower oils. The pure triacylglycerols highly enriched for CLA (90–96 percent) may be confirmed by H NMR. Esterification proceeds using immobilized *Candida antarctica* Lipase. Preferably, the CLA will contain at least 40 and upwardly 45–48 percent of c9,t11-octadecadienoic and t10, c12-octadecadienoic acids, and mixtures thereof. There will be less than one percent esters 8,10; 11,13; and trans, trans isomers or less than five percent in the aggregate. The resultant triacylglycerol is not purified further to remove all levels of phosphatidyl and sterol residues. But those levels remaining from isomerization of sunflower and safflower oils will be adequate for commercial applications involving safe, edible products in feed and food.

The immobilized *Candida antarctica* lipase is to be employed in a manner similar to that described for n-3 type polyunsaturated fatty acids, in Harraldson et al. The esterification reaction is conducted at 50–75° C., preferably 65 ° C., in the absence of any solvent and a vacuum employed in order to remove the co-produced water or alcohols (from esters) upon formation. This shifts the triacylglycerol production to completion and ensures a highly pure product virtually free of any mono- and diacylglycerols in essentially quantitative yields. Stoichiometric amounts of free fatty acids may be used, i.c. 3 molar equivalents as based oil glycerol or 1 molar equivalent as based on number of mol equivalents of hydroxyl groups present in the glycerol moiety. Only 10% dosage of lipase as based on total weight of substrates is needed, which can be used a number of times. This is very important from the productivity point of view. All this, together with the fact that no solvent is required, renders this process a high feasibility from the scaling-up and industrialization point of view, since the cut in volume and bulkiness is enormous. Also, a slight excess (<5/5) of free fatty acids may be used in order to speed up the reaction toward the end and ensure a completion of the reaction.

At the initiation of the reaction, the 1- or 3-monoacyglyeride is formed first, followed by the 1,3 diacylglyeride, and finally the triglyceride at the more extended reaction times. The mono- and diacylglyerides are useful intermediates in that they manifest biological activity, but have greater soluability in aqueous cellular environments and can participate in alternative molecular synthetic pathways such as synthesis of phospholipids or other funtional lipids. In contrast, triglycerides are frequently deposited intact in cell membranes or storage vesicles. Thus, the administration of CLA in mono-, di- or triglycerol form rather than free fatty acid or ester, may influence the mode and distribution of uptake, metabolic rate and structural or physiological role of the CLA component.

In one preferred embodiment, administration is oral. The CLA may be formulated with suitable carriers such as starch, sucrose or lactose in tablets, pills, dragees, capsules, solutions, liquids, slurries, suspensions and emulsions. The CLA may be provided in aqueous solution, oily solution, or in any of the other forms discussed above. The tablet or capsule of the present invention may be coated with an enteric coating which dissolves at a pH of about 6.0 to 7.0. A suitable enteric coating which dissolves in the small intestine but not in the stomach is cellulose acetate phthalate. In some embodiments, the CLA is provided as soft gelatin capsules containing 750 mg 80% CLA (Tonalin™). The CLA may also be provided by any of a number of other routes, including, but not limited to, intravenous, intramuscular, intra-arterial, intramedullary, intrathecal, intraventricular, transdermal, subcutaneous, intraperitoneal, intranasal, enteral, topical, sublingual or rectal means. Further details on techniques for formulation for and administration and administration may be found in the latest edition of *Remington's Pharmaceutical Sciences* (Maack Publishing Co., Easton, Pa.).

An effective amount of CLA may also be provided as a supplement in various prepared food products and drinks. For the purposes of this application, prepared food product means any natural, processed, diet or non-diet food product to which CLA has been added. The CLA may be added in the form of free fatty acids or as an oil containing partial or whole triglycerides of CLA. Therefore, CLA may be directly incorporated into various prepared food products, including, but not limited to diet drinks, diet bars, supplements, prepared frozen meals, candy, snack products (e.g., chips), prepared meat products, milk, cheese, yogurt and any other fat or oil containing foods.

CLA is susceptible to oxidation. Therefore, it is desirable to package CLA for human use with suitable antioxidants such as lecithin, tocopherols, ascorbate, ascorbyl palmitate or spice extracts such as rosemary extract.

EXAMPLES

Example 1

Isomerization of Safflower Oil Using Propylene Glycol at Low Temperature

Safflower oil was isomerized in propylene glycol at low temperatures using KOH as a catalyst. The isomerization apparatus consisted of a two-necked flask with a thermometer placed in one neck, leaving a small opening to release excess pressure. A nitrogen supply was attached to the other neck of the flask. Solutions added to the flask were agitated by the use of a magnetic bar and a magnetic stirrer. The temperature of the flask was controlled by placing the flask in a thermostat-controlled oil bath placed on the magnetic stirrer.

The flask was filled with 60.27 g propylene glycol and 28.20 g KOH and immersed into the oil bath. The temperature was increased to 130° C. to dissolve the KOH. After the KOH had dissolved, 60.09 g of safflower oil was introduced into the flask. A high volume of nitrogen was circulated through the two-neck flask for 5 min. and then reduced to a lower volume. The mixture was heated to 150° C., which took approximately 40 min. The mixture was then allowed to react at 150° C. for 3.5 hours. At intervals, 3ml samples were withdrawn for analysis.

The samples were placed directly into 6 ml of hot water and citric acid was added in excess until the free fatty acids separated out as the top layer. Heating was necessary to prevent solidification while the citric acid was added. To convert the free fatty acids into methylesters for analysis by Gas Chromatography, 0.025 g of the free fatty acids, 5 ml of a 4% solution of HCl and ethanol were added to a test tube. Nitrogen was added to the tube, then the tube was sealed and placed in a water bath at 60° C. for 20 min. The tube was then cooled and 1 ml purified water and 5 ml isooctane were added. Nitrogen was added to the tube and the tube was shaken for 30 seconds. The resulting upper layer was added to till of purified water in a new test tube and again shaken under nitrogen. The resulting upper layer was then washed of isooctane and decanted into a third test tube. A small amount of sodium sulfate was added for water absorption. A 1 µl sample was then injected directly into the Gas chromatograph.

The gas chromatography conditions were as follows:

| | |
|---|---|
| System: | Perkins-Elmer Auto System |
| Injector: | Splitless at 240° C. |
| Detector: | Flame Ionization Detector at 280° C. |
| Carrier: | Helium |
| Column: | WCOT Fused Silica 0.25 mm X100M, CP-SL 88 for FAME, DF 0.2 |
| Oven Program: | 80° C. (0 min.) increasing to 220° C. at 10° C. per min. and held at 220° C. for 10 min. |

All results are expressed as the relative peak area percentage. Standards are generally unavailable, so the peaks which eluted were verified with other systems. GC-MS determines the number, but not the position of cis and trans bonds. Therefore, NMR analysis was used to verify the bond positions. The main peaks were c9,t11 and t10,c12. For NMR analysis of CLA isomers, please see Marcel S. F. Lie Ken Jie and J. Mustafa, *Lipids*, 32 (10) 1019–34 (1997), incorporated herein by reference.

This data, presented in Table 6 and summarized in Table 10, demonstrates that isomerizationi of safflower oil using polypropylene glycol as a solvent, KOH as a catalyst, and low temperatures results in the production of conjugated linoleic acid lacking 8,10 and 11,13 isomers. The highly polar columns utilized in this experiment may be successfully used to separate the 8,10 and 11,13 isomers from c9,t11 and t10,c12 isomers. The 8,10 isomers tend to coelute or elute just after the c9,t11 isomer. The 11,13 isomer elutes in front of the t10,c11 isomer or coelutes with the t10,c12 isomer, depending on the column conditions.

The conjugated linoleic acid produced according to this method by characterized by comparing the various isomers produced. First, the isomerization reaction went essentially to completion. The completeness of the reaction is obtained by dividing the total peak area the for linoleic acid isomers minus residual c9,t12 linoleic acid by the total peak area. This value is 0.994. Second, the ratio of c9,t11 and t10,c12 isomers to total peak area may be determined. This value is 0.953. Third, the ratio of the t9,t11 and t10,t12 isomers to the c9,t11 and t10,c12 isomers may be determined. This value is 0.010. Fourth, the ratio of the t9,t11 and t10,t12 isomers to total peak area may be determined. This value is 0.009. Fifth, the ratio of the t10,c12 isomer to the c9,t11 isomer may be determined. This value is 1.018. These ratios are summarized in Table 11.

Example 2

Aqueous Isomerization at High Temperature and Pressure

Fifty grams of water and 25.32 g NaOH were added to a high pressure reactor (Parr Model 450 ML Benchtop Alloy 400, equipped with a pressure gauge and stirrer.) The NaOH was allowed to dissolve and 94.0 g safflower oil was added to the reactor. The reactor was closed and flushed for 2 min. with nitrogen and then all valves were closed. The reactor was heated in an electrical gasket to 210° C. and maintained at that temperature for 6 hours. The temperature was then reduced to 60° C. before pressure was released and the reactor opened. Two grams of the resulting solidified soap were taken from the reactor and dissolved in water at approximately 40° C. Citric acid was then added to reduce the pH of the solution to below 6. A sample was withdrawn from the fatty acid top layer and prepared for Gas Chromatography as in Example 1.

The results of the gas chromatography are presented in Table 7 and summarized in Table 10. These data indicate that this isomerization method results in the formation of relatively high amounts of the 8,10 and 11,13 isomers. Ratios are presented in Table 11.

Example 3

Non-aqueous Alkali Isomerization of Safflower Oil at High Temperature and Pressure 100.48 g propylene glycol and 46.75 g of KOH were added to a high-pressure reactor as described in Example 2. The reactor was then heated to 130° C. to dissolve the KOH. 100.12 g of safflower oil were then added to the KOH-propylene glycol mixture. The reactor was closed, flushed for 1 min. with nitrogen, and all valves closed. The reactor was then heated to 210° C. and maintained at that temperature for 1 hour. The reactor was cooled and the contents decanted into 120 g of hot water. While stirring, 35.3 g 37% HCl and 27.59 g citric acid were serially added to the fatty acids. A sample was taken from the top layer and dried in a vacuum flask at 60° C. A sample of the resulting fatty acids was analyzed by gas chromatography as described in Example 1.

The results are presented in Table 8 and summarized in Table 10. This experiment demonstrates that isomerization of safflower oil with KOH and a non-aqueous solvent at high temperature results in the formation of significant amounts of 8,10 and 11,13 isomers, as well as t9,t11 and t10,t12 isomers. Ratios are presented in Table 11.

Example 4

Aqueous Alkali Reaction at Low Temperature 49.94 g water and 39.96 g NaOH were added to a high-pressure reactor as described in Example 3. This mixture was heated until the NaOH dissolved. Next, 100.54 g of safflower oil was added to the high-pressure reactor, the reactor was flushed with nitrogen, and all valves closed. The high-pressure reactor was heated to 179° C. for 22.5 hours.

Samples were prepared for Gas Chromatography as in Example 3. The data is provided in Table 9 and summarized in Table 10. This experiment demonstrates that when low temperatures are used for aqueous alkali isomerization, the conjugation reaction does not go to completion. Furthermore, significant amounts of the 8,10 and 11,13 isomers are produced. Ratios are presented in Table 11.

TABLE 6

| Peak # | Time (Min) | Component Name | Area (%) | Area ($\mu$V.s) | Height ($\mu$V) |
|---|---|---|---|---|---|
| 1 | 38.164 | | 0.08 | 4101.65 | 622.28 |
| 2 | 49.539 | C16:0 | 6.29 | 335897.80 | 32745.95 |
| 3 | 53.107 | C16:1 | 0.06 | 3240.60 | 447.82 |
| 4 | 61.620 | C18:0 | 2.38 | 127182.30 | 12999.14 |
| 5 | 64.821 | C18:1 c9 | 12.34 | 659111.72 | 52209.40 |
| 6 | 65.254 | | 0.57 | 30402.68 | 3475.09 |
| 7 | 67.263 | | 0.11 | 5757.35 | 758.08 |
| 8 | 67.940 | | 0.10 | 5523.00 | 700.44 |
| 9 | 68.755 | | 0.24 | 12816.90 | 1543.27 |
| 10 | 69.310 | | 0.22 | 11803.80 | 1430.59 |
| 11 | 69.846 | C18:2 c9,c12 | 0.44 | 23336.75 | 2500.24 |
| 12 | 73.618 | | 0.28 | 14828.70 | 1838.66 |
| 13 | 76.621 | | 0.16 | 8400.65 | 1050.19 |
| 14 | 77.388 | CLA c9,t11 | 36.51 | 1950669.98 | 124313.83 |
| 15 | 78.370 | CLA t10,c12 | 37.16 | 1985488.96 | 132265.33 |
| 16 | 78.664 | CLA c9,c11 | 1.06 | 56583.10 | 5699.43 |
| 17 | 78.880 | CLA c10,c12 | 1.26 | 67503.55 | 4572.65 |
| 18 | 80.102 | CLA t9,t11/ t10,t12 | 0.73 | 39110.00 | 4743.28 |
| 19 | 85.165 | | 0.03 | 1621.65 | 231.32 |
| | | | 100.00 | 5343381.15 | 384147.01 |

TABLE 7

| Peak # | Time (Min) | Component Name | Area (%) | Area ($\mu$V.s) | Height ($\mu$V) |
|---|---|---|---|---|---|
| 1 | 36.554 | | 0.09 | 4122.05 | 627.02 |
| 2 | 47.785 | C16:0 | 6.68 | 290571.30 | 28224.34 |
| 3 | 51.280 | C16:1 | 0.07 | 3188.05 | 425.57 |
| 4 | 59.787 | C18:0 | 2.63 | 114362.95 | 12678.63 |
| 5 | 62.923 | C18:1 c9 | 13.12 | 570712.08 | 42259.71 |
| 6 | 63.346 | | 0.72 | 31329.22 | 3774.35 |
| 7 | 65.355 | | 0.54 | 23620.70 | 2848.31 |
| 8 | 66.034 | | 0.67 | 28890.78 | 3333.95 |
| 9 | 66.574 | | 0.10 | 4370.91 | 594.22 |
| 10 | 66.811 | | 0.35 | 15045.61 | 1469.30 |
| 11 | 67.352 | | 0.41 | 18002.20 | 2035.53 |
| 12 | 67.889 | C18:2 c9,c12 | 1.43 | 62002.15 | 6714.22 |
| 13 | 69.200 | | 0.09 | 3840.85 | 474.10 |
| | | | | | 474.10 |
| 14 | 71.680 | | 0.30 | 13099.10 | 1744.21 |
| 15 | 74.640 | | 1.62 | 70689.87 | 4117.23 |
| 16 | 75.310 | CLA c9,t11/ 8,10 | 24.87 | 1082087.96 | 57619.24 |
| 17 | 76.032 | CLA 11,13 | 14.72 | 640440.14 | 42975.86 |
| 18 | 76.277 | CLA t10,c12 | 16.00 | 695923.85 | 63512.81 |
| 19 | 76.450 | CLA c8,c10 | 1.26 | 54676.10 | 7614.29 |
| 20 | 76.626 | CLA c9,c11 | 2.08 | 90411.44 | 10891.36 |
| 21 | 76.881 | CLA c10,c12 | 3.00 | 130593.96 | 11727.80 |
| 22 | 77.022 | CLA c11,c13 | 1.77 | 77065.69 | 9906.74 |
| 23 | 77.477 | | 0.66 | 28867.85 | 3322.69 |
| 24 | 77.868 | | 0.63 | 27391.94 | 2934.68 |
| 25 | 78.173 | CLA t9,t11/ t10,t12 | 6.00 | 260985.40 | 26124.10 |
| 26 | 83.140 | | 0.12 | 5164.40 | 586.21 |
| 27 | 85.878 | | 0.06 | 2735.80 | 347.01 |
| | | | 100.00 | 4350282.35 | 348883.46 |

TABLE 8

| Peak # | Time (Min) | Component Name | Area (%) | Area ($\mu$V.s) | Height ($\mu$V) |
|---|---|---|---|---|---|
| 1 | 38.249 | | 0.08 | 3999.70 | 599.26 |
| 2 | 49.639 | C16:0 | 6.41 | 333807.80 | 32279.13 |
| 3 | 53.218 | C16:1 | 0.06 | 3123.00 | 427.39 |
| 4 | 55.508 | | 0.03 | 1322.20 | 190.60 |
| 5 | 61.753 | C18:0 | 2.55 | 132854.50 | 14939.09 |
| 6 | 64.104 | C18:1 c9 | 0.03 | 1640.30 | 245.73 |
| 7 | 64.950 | | 12.92 | 672672.91 | 53345.47 |
| 8 | 65.382 | | 0.64 | 33297.29 | 3728.28 |
| 9 | 65.783 | | 0.03 | 1411.20 | 219.76 |
| 10 | 67.403 | | 0.62 | 32194.66 | 2836.09 |
| 11 | 67.793 | | 0.24 | 12660.05 | 1495.10 |
| 12 | 68.088 | | 0.68 | 35371.43 | 3210.82 |
| 13 | 68.421 | | 0.07 | 3684.10 | 473.77 |
| 14 | 68.635 | | 0.04 | 1948.63 | 257.65 |
| 15 | 68.890 | | 0.29 | 14979.18 | 1499.63 |
| 16 | 69.192 | | 0.04 | 2268.69 | 324.39 |
| 17 | 69.430 | | 0.25 | 13028.21 | 1369.93 |
| 18 | 69.947 | C18:2 c9,c12 | 0.23 | 11895.70 | 1125.77 |
| 19 | 70.341 | | 0.02 | 1168.20 | 196.75 |
| 20 | 73.741 | | 0.31 | 15930.60 | 1965.82 |
| 21 | 75.448 | | 0.08 | 3906.00 | 387.98 |
| 22 | 76.768 | | 1.79 | 93172.74 | 6637.34 |
| 23 | 77.002 | | 0.63 | 32882.76 | 5024.06 |
| 24 | 77.389 | CLA c9,t11/ 8,10 | 15.62 | 813447.45 | 57234.62 |
| 25 | 77.735 | | 1.92 | 99754.50 | 8641.88 |
| 26 | 78.045 | CLA 11,13 | 4.03 | 209728.35 | 19826.20 |
| 27 | 78.335 | CLA t10,c12 | 12.63 | 657681.44 | 62016.93 |
| 28 | 78.566 | CLA c8,c10 | 0.64 | 33432.80 | 5277.06 |
| 29 | 78.727 | CLA c9,c11 | 2.21 | 114935.49 | 10791.54 |
| 30 | 79.079 | CLA c10,c12 | 3.98 | 207339.28 | 12766.61 |
| 31 | 79.663 | CLA c11,c13 | 1.40 | 73036.34 | 6275.58 |
| 32 | 80.516 | CLA t9,t11/ t10,t12 | 29.39 | 1529956.09 | 100323.85 |
| 33 | 82.318 | | 0.03 | 1563.70 | 230.42 |
| 34 | 85.289 | | 0.07 | 3657.50 | 423.53 |
| 35 | 88.093 | | 0.05 | 2368.50 | 301.03 |
| | | | 100.00 | 5206121.30 | 416889.05 |

TABLE 9

| Peak # | Time (Min) | Component Name | Area (%) | Area ($\mu$V.s) | Height ($\mu$V) |
|---|---|---|---|---|---|
| 1 | 38.154 | | 0.09 | 3371.70 | 501.86 |
| 2 | 49.501 | C16:0 | 6.80 | 253221.00 | 25807.11 |
| 3 | 53.100 | C16:1 | 0.07 | 2723.55 | 353.01 |
| 4 | 55.391 | | 0.03 | 1078.10 | 142.65 |
| 5 | 61.618 | C18:0 | 2.68 | 100015.20 | 11002.94 |
| 6 | 63.990 | | 0.03 | 946.40 | 156.50 |
| 7 | 64.791 | C18:1 c9 | 13.13 | 489016.55 | 38313.02 |
| 8 | 65.270 | | 0.69 | 25645.55 | 2670.46 |
| 9 | 67.296 | | 0.12 | 4466.65 | 558.35 |
| 10 | 67.960 | | 0.11 | 4012.70 | 517.76 |
| 11 | 68.800 | | 0.37 | 13840.49 | 1314.91 |
| 12 | 69.370 | | 0.30 | 11141.11 | 1245.85 |
| 13 | 70.001 | C18:2 c9,c12 | 20.52 | 764287.35 | 62474.10319.72 |
| 14 | 73.538 | | 0.30 | 11075.20 | 1357.19 |
| 15 | 76.519 | | 0.42 | 15662.14 | 1154.22 |
| 16 | 77.231 | CLA c9,t11/ 8,10 | 22.45 | 836230.58 | 56972.76 |
| 17 | 77.911 | CLA 11,13 | 7.56 | 281633.54 | 24467.27 |
| 18 | 78.197 | CLA t10,c12 | 19.77 | 736384.86 | 66688.46 |
| 19 | 78.559 | CLA c8,c10 | 1.21 | 45158.40 | 3837.29 |
| 20 | 78.787 | CLA c9,c11 | 0.87 | 32564.06 | 3409.07 |
| 21 | 78.953 | CLA c10,c12 | 0.89 | 33053.57 | 2499.70 |
| 22 | 79.413 | CLA c11,c13 | 0.12 | 4453.10 | 353.06 |
| 23 | 79.792 | | 0.13 | 4936.60 | 436.59 |
| 24 | 80.052 | CLA t9,t11/ t10,t12 | 1.13 | 42203.55 | 4550.59 |

TABLE 9-continued

| Peak # | Time (Min) | Component Name | Area (%) | Area ($\mu$V.s) | Height ($\mu$V) |
|---|---|---|---|---|---|
| 25 | 82.298 | | 0.03 | 981.60 | 150.46 |
| 26 | 82.946 | | 0.03 | 1107.95 | 151.48 |
| 27 | 85.135 | | 0.10 | 3639.90 | 383.36 |
| 28 | 87.927 | | 0.06 | 2212.50 | 254.61 |
| | | | 100.00 | 3725063.90 | 311570.23 |

TABLE 10

Relative Area Percentage

| Isomer | Example 1 | Example 2 | Example 3 | Example 4 |
|---|---|---|---|---|
| c9,t12 | 0.44 | 1.43 | 0.23 | 20.52 |
| c9,t11 | 36.51 | na | na | na |
| c9,t11/8,10 | <0.5* | 24.87 | 15.62 | 22.45 |
| t10,c12 | 37.16 | 16.00 | 12.63 | 19.77 |
| c9,c11 | 1.06 | 2.08 | 2.21 | 0.87 |
| c8,c10 | <0.5 | 1.26 | 0.64 | 1.21 |
| c10,c12 | 1.26 | 3.00 | 3.98 | 0.89 |
| t9,t11/t10,t12 | 0.73 | 6.00 | 29.39 | 1.13 |
| 11,13 | <0.5 | 10.23 | 4.05 | 7.65 |
| c11,c13 | <0.5 | 1.77 | 1.40 | 0.12 |
| Unidentified | <0.5 | 2.91 | 4.34 | 0.55 |
| CLA Total | 76.88 | 72.61 | 74.24 | 54.55 |
| Total area | 77.32 | 74.04 | 74.47 | 75.07 |

*total percentage of 8,10 is less than 0.5
na- value is reflected as component of c9,t11/8,10

TABLE 11

| Isomer | Ratio | Example 1 | Example 2 | Example 3 | Example 4 |
|---|---|---|---|---|---|
| Total CLA isomer | Total peak area | 0.994 | 0.981 | 0.997 | 0.727 |
| c9,t11-t10,c12 | Total peak area | 0.953 | 0.552* | 0.379* | 0.562* |
| t9,t11-t10,t12 | c9,t12-t10,c12 | 0.010 | 0.147* | 1.040* | 0.027* |
| t9,t11-t10,t12 | Total peak area | 0.009 | 0.081 | 0.395 | 0.015 |
| Total 11,13 area | Total peak | na | 0.223 | 0.073 | 0.102 |
| t10,c12 | c9,t11 | 1.018 | 1.554* | 0.809* | 0.881* |

*c9,t11 includes 8,10 isomer
na- no 11,13 detected

Example 5
The Preparation of Triacylglycerols of CLA by Direct Esterification General. H nuclear magnetic resonance spectra were recorded on a Bruker AC 250 NMR spectrometer in deuterated chloroform as a solvent. HPLC separations were carried out by a PrepLC™ System 500A instrument from Waters using the PrepPak® 500/Silica Cartridge column from Millipore, eluting with 10% diethyl ether in petroleum ether. Analytical GLC was conducted on a Perkin-Elmer 8140 Gas Chromatograph according to a previously described procedure, as described in Haraldsson, et al., Acta Chem Scanned 45:723 (1991).

The immobilized *Candida antarctica* lipase was provided by Novo Nordisk in Denmark as Novozyme™. It was used directly as provided in the esterification experiments. Analytical grade diethyl ether purchased from Merck was used without any purification, but synthetic grade n-hexane also from Merck was freshly distilled prior to use in extractions and HPLC chromatography. Glycerol (99%) was purchased from Sigma and Aldrich Chemical Company and used without further purification. The CLA concentrate was provided by Natural Lipids in Norway as free fatty acids as Tonalin™. Its purity was confirmed by analytical GLC and high-field NMR spectroscopy which revealed some glyceride impurities. The CLA concentrate was found to contain 43.3% 9-cis,11-trans-linoleic acid, 44.5% 10-trans,12-cis-linoleic acid, 5.4% of other CLA isomers, 5.6% oleic acid and 0.6% each of palmitic and stearic acid as determined by GLC at the Science Institute.

Example 6
The Preparation of Triacylglycerols of CLA by Direct Esterification Immobilized *Candida antarctica* lipase (1.25 g) was added to a mixture of glycerol (1.22 g, 13.3 mmol) and CLA as free fatty acid (M.wt.280.3 g/mol; 11.6 g, 41.5 mmol). The mixture was gently stirred on a magnetic stirrer hot plate at 65° C. under continuous vacuum of 0.01–0.5 Torr. The volatile water produced during the progress of the reaction was continuously condensed into liquid nitrogen cooled traps. After 48 h the reaction was discontinued, n-hexane added and the enzyme separated off by filtration. The organic phase was treated with an alkaline aqueous solution of sodium carbonate to remove excessive free fatty acids (when required). The organic solvent (after drying over anhydrous magnesium sulfate when appropriate) was removed in vacuo on a rotary evaporator followed by high-vacuum treatment to afford the virtually pure product as a slightly yellowish oil (10.9 g; average M.wt.878.6 g/mol; 93% yield). When stoichiometric amounts of free fatty acids were used, titration by standardized sodium hydroxide was applied to determine the free fatty acid content of the crude reaction product (less than 1% free fatty acid content as based on number of mol of ester groups, corresponding to at least 99% incorporation, which is equivalent to the minimum of 97% triglyceride content). The crude product was directly introduced into HPCL eluting with 10% diethylether in n-hexane to afford 100% pure triglyceride as a colourless oil. 250 MHz 1H NMR (CDC13) 8 (ppm) 6.35–6.23 (3H, ddt, Jtrans=15.0 Hz, J=10.9 Hz, Jally1=1.3,=CHCH=CH), 5.98–5.90 (3H, dd, Icis=10.9, J=10.9, —CH=CHCH=), 5.71–5.50 (3H dtd, Jtrans=15.0 Hz, J=6.9 Hz, J=6.9 Hz, J=2.2 Hz, =CH=CHCH2—), 5.35–5.26 (4H, m, =CH2CH=CH— and —CH2C—ICH2—), 4.33–4.26 (2H, dd, Jgem=11.9 Hz, J=4.3, —CH2CHCH2—), 4.18–4.10 2H, dd, Jgem=1.8 Hz, J=6.0, —CH2CHCH2—), 2.37–2.31 (6H, t, J=7.4 H2, —CH2COOR), 2.19–2.05 (12H, m, —CH2CH=CH—), 1.66–1.60 (6H, qu., J=Hz, —CH2CH2COOR), 1.43–1.30 (18H, m, —CH2—), 0.91–0.86 (9H, t, J=6.7 Hz, —CH3). 13C-NMR (CDC13): 8 (ppm) 173.2, 172.8, 134.6, 130.0, 128.6, 125.5, 68.8, 62.0, 34.0, 32.9, 31.6, 29.6–28.9 (6C), 27.6, 24.8, 22.5, 14.1.

In order to monitor the progress of the reaction and provide more details about the composition of individual glycerides during the reaction, samples were collected regularly as the reaction proceeded. They were analyzed by HNMR spectroscopy and provided a good insight into the composition of mono-, di- and triacylglycerols during the progress of the reaction. The results are demonstrated in Table 12 below. As can be noticed from the table, 1,3-diacylglycerols dominated the reaction mixture during the first two hours of the reaction. After 4 hours triacylglycerols took over and had reached 98% composition after 22 hours and 100% after 48 hours. As would be expected 1,2-diacylglycerols reached considerably lower levels than the 1,3-diacylglycerols. 1-monoacylglycerols reached a maximum during the first hour of the reaction, but 2-monoacylglycerols were not detected throughout the reaction.

TABLE 12

| Time | % Incorporation | | | | Residual FFA |
|---|---|---|---|---|---|
| h | 1-MG | 1,2-DG | 1,3-DG | TG | % |
| 0 | 0 | 0 | 0 | 0 | 100 |
| 1 | 8.3 | 15.2 | 39.4 | 7.8 | 29.3 |
| 2 | 2.7 | 9.3 | 46.5 | 17.4 | 24.1 |
| 4 | 1.7 | 7.9 | 25.4 | 49.4 | 15.5 |
| 6 | 0.5 | 5.2 | 16.0 | 68.1 | 10.1 |
| 8 | 0.0 | 3.9 | 9.9 | 80.5 | 5.7 |
| 10 | 0.0 | 3.0 | 7.0 | 85.8 | 4.2 |
| 12 | 0.0 | 2.7 | 5.6 | 89.2 | 2.5 |
| 22 | 0.0 | 1.0 | 1.4 | 95.8 | 1.8 |
| 48 | 0.0 | 0.0 | 0.0 | 100 | 0.0 |

Example 7
Effect of Varying Temperature and Reaction Duration on CLA Yield and Composition The effect of temperature and reaction duration on the conjugation of safflower oil was determined. Water and NaOH were added to a high pressure reactor (Parr Model 450 ML Benchtop Alloy 400, equipped with a pressure gauge and stirrer) as indicated in Table 13, columns 1 and 2. The NaOH was allowed to dissolve and safflower oil (column 3) was added to the reactor. The reactor was closed and flushed for 2 min. with nitrogen and then all valves were closed. The reactor was heated in an electrical gasket to the desired temperature (column 4) and maintained at that temperature for the desired time (column 5). The temperature was then reduced to 60° C. before pressure was released and the reactor opened. For each reaction, two grams of the resulting solidified soap were taken from the reactor and dissolved in water at approximately 40° C. Citric acid was then added to reduce the pH of the solution to below 6. A sample was withdrawn from the fatty acid top layer and prepared for Gas Chromatography.

The results of the gas chromatography are presented in column 6 (total percentage of 9,11 and 10,12 isomers), column 7 (total percentage of 11,13 isomers), and column 8 (total percentage of all CLA isomers or yield). These data indicate that as reaction duration and temperature increase, the total amount of conjugation and the percentage of 11,13 isomers increase. Under conditions where formation of the 11,13 isomer is low, the total amount of conjugation is also low.

TABLE 13

| Water gram | NaOH gram | Safflower Oil gram | Mean t, ° C. of reaction | Time hours | 9,11 + 10,12 area % | 11,t3 area % | CLA total area % |
|---|---|---|---|---|---|---|---|
| 50.21 | 29.93 | 99.94 | 189 | 6.36 | 45.99 | 5.73 | 55.86 |
| 70.20 | 29.93 | 99.94 | 187 | 6.40 | 44.94 | 3.23 | 51.28 |
| 50.10 | 30.17 | 100.74 | 183 | 6.39 | 40.23 | 3.37 | 48.07 |
| 49.91 | 29.93 | 100.40 | 179 | 6.52 | 32.00 | 1.48 | 34.92 |
| 49.97 | 29.80 | 100.02 | 179 | 10.08 | 41.86 | 3.12 | 48.21 |
| 49.94 | 39.84 | 99.84 | 179 | 6.30 | 32.6 | 3.04 | 37.12 |
| 29.50 | 24.83 | 99.21 | 240 | 3.25 | 28.37 | 10.78 | 71.58 |
| 30.33 | 25.15 | 100.43 | 221 | 2.30 | 40.87 | 14.72 | 72.61 |
| 49.92 | 30.00 | 100.36 | 150 | 6.34 | 7.07 | 0 | 7.44 |

Example 8
Conjugation of Safflower Fatty Acid Methylester (FAME)

The reaction was carried out in a closed vessel. The following components were mixed together: 10 g safflower FAME and a mixture of approximately 2.8 g $KOCH_3$ and 2.8 g methanol. There was probably more KOMe than methanol due to evaporation of methanol during mixing of the two components. The mixture was stirred for 5 hours at 111–115 deg C. in nitrogen atmosphere in a closed reaction vessel. The distribution of isomers was analyzed by Gas Chromatography. The results are summarized in Table 14. These data indicate that the conjugation safflower FAME may be accomplished under mild conditions, resulting in a product lacking appreciable amounts of undesirable 8,10 and 11,13 isomers.

TABLE 14

| Isomer Distribution | |
|---|---|
| Palmitic acid | 6.6% |
| Stearic acid | 2.7% |
| Oleic acid | 12.9% |
| Linoleic acid | 5.7% (unconjugated) |
| CLA c9,t11 | 34.1% |
| CLA t10,c12 | 33.3% |
| CLA c,c | 1.8% |
| CLA t,t | 1.0% |
| CLA total | 70.2% |

Example 9
Large Scale Batch Production of Conjugated Safflower FAME

The production of safflower conjugated FAME may be divided into two steps, methanolysis and conjugation. For methanolysis, 6,000 kg safflower oil was drawn into a closed reactor. The reactor was purged with nitrogen at atmospheric pressure, and 1150 liters of methanol and 160 kg of $NaOCH_3$ (30% solution) were added. The mixture is heated to 65° C. while stirring, and reacted at 65° C. for 2 hours. The resulting bottom layer was decanted while the reactor was purged with nitrogen gas. 1000 liters of water (40–50° C., into which 50 kg citric acid monohydrate has been dissolved) was then added while stirring. The layers were allowed to separate (approx. 60 min.) and the bottom layer decanted while purging the reactor with nitrogen gas. The resulting safflower FAME product was dried at 80° C. under vacuum for one hour.

To conjugate the safflower FAME, 250 kg of $KOCH_3$ dissolved in methanol to form a paste was added to the reactor. The mixture was then heated to 120° C. while stirring and the reaction allowed to continue for 3 hours. The mixture was cooled to 100° C., and 1000 liters of water (40–50° C., into which 50 kg citric acid monohydrate has been dissolved) was added while stirring. The mixture was stirred for 15 minutes and then the layers were allowed to separate for 20 minutes. The bottom layer was decanted and the product dried at 80° C. for 1 hour and then stored under nitrogen.

The resulting CLA was analyzed using a Perkin Elmer Autosystem XL GC under the following conditions:

| Column: | WCOT Fused Silica 100 m × 0.25 mm, Coating CP SIL 88 |
| --- | --- |
| Carrier: | He gas, 30.0 PSI |
| Temp: | 220 C. |
| Run time: | 35–90 min. |
| Inject.: | Splitless, 240 C. |
| Detect.: | FID, 280 C. |

The GC results are summarized in Tables 15 and 16.

TABLE 15

| Peak # | Time (min) | Component Name | Area (%) | Area ($\mu$Vs) | Height ($\mu$V) |
| --- | --- | --- | --- | --- | --- |
| 1 | 46.874 | C16:0 | 6.37 | 29874.50 | 4026.29 |
| 2 | 58.685 | C18:0 | 2.61 | 12231.70 | 1542.34 |
| 3 | 62.141 | C18:1 c9 | 13.14 | 61668.78 | 7369.08 |
| 4 | 62.652 |  | 0.70 | 3263.62 | 391.92 |
| 5 | 66.404 |  | 0.35 | 1627.60 | 177.41 |
| 6 | 66.917 |  | 0.26 | 1239.15 | 157.35 |
| 7 | 67.583 | C18:2 c9,c12 | 5.75 | 26964.95 | 3153.80 |
| 8 | 70.631 |  | 0.25 | 1171.90 | 141.41 |
| 9 | 75.011 | CLA c9,t11 | 34.42 | 161529.90 | 17544.79 |
| 10 | 75.936 | CLA t10,c12 | 33.48 | 157129.82 | 17157.21 |
| 11 | 76.400 | CLA c9,c11 | 0.84 | 3935.70 | 302.61 |
| 12 | 76.631 | CLN c10,c12 | 0.49 | 2316.98 | 279.31 |
| 13 | 77.905 | CLA t, t9,11 + 10,12 | 1.35 | 6344.50 | 710.88 |
|  |  |  | 100.00 | 469299.10 | 52954.41 |

TABLE 16

| Peak # | Time (min) | Component Name | Area (%) | Area ($\mu$Vs) | Height ($\mu$V) |
| --- | --- | --- | --- | --- | --- |
| 9 | 75.011 | CLA c9, t11 | 48.76 | 161529.90 | 17544.79 |
| 10 | 75.936 | CLA t10, c12 | 47.43 | 157129.82 | 17157.21 |
| 11 | 76.400 | CLA c9, c11 | 1.19 | 3935.70 | 302.61 |
| 12 | 76.631 | CLA c10, c12 | 0.70 | 2316.98 | 279.31 |
| 13 | 77.905 | CLA t, t 9, 11 + 10, 12 | 1.92 | 6344.50 | 710.88 |
|  |  |  | 100.00 | 331256.90 | 35994.80 |

Example 10

The following are examples of typical animal rations containing the CLA free fatty acids, triglycerides, and esters of the present invention.

A. Pig Starter Rations

TABLE 17

| Ingredients | lbs. | kgs. |
| --- | --- | --- |
| Corn, yellow (8.4% protein) | 1067 | 484.7 |
| Soy bean meal, solvent extracted, dehulled (47% protein) | 570 | 259 |
| CLA | 5 | 2.3 |
| Whey, dried (12.0% protein) | 300 | 136 |
| Dicalcium phosphate | 24 | 11 |
| Limestone | 16 | 7 |
| Iodized salt | 5 | 2 |
| Trace mineral premix | 5 | 2 |
| Vitamin premix | 8 | 4 |
| Totals | 2000 | 908 |

B. Grower-Finisher Rations for Pigs (from 40–240 LBS [18–109 KGS])

TABLE 18

| Ingredients | lbs. | kgs. |
| --- | --- | --- |
| Corn, yellow (8.4% protein) | 1566 |  |
| Soybean meal, solvent extracted (44% protein) | 380 |  |
| CLA | 5 |  |
| Dicalcium phosphate | 21 |  |
| Limestone | 15 |  |
| Iodized Salt | 5 |  |
| Trace Mineral Premix | 3 |  |
| Vitamin Premix | 3 |  |
| Total | 2000 |  |

C. Pig Grower Finisher Rations (for Pigs 121–240 LBS [55–109 KGS])

TABLE 19

| Ingredients | lbs. | kgs. |
| --- | --- | --- |
| Corn, yellow (8.4% protein) | 1687 |  |
| Soybean meal, solvent extracted (44% protein) | 265 |  |
| CLA | 5 |  |
| Dicalcium phosphate | 18 |  |
| Limestone | 15 |  |
| Iodized salt | 5 |  |
| Trace mineral premix | 2 |  |
| Vitamin premix | 3 |  |
| Total | 2000 |  |

Composition and Analysis of Pig Trace Mineral Remix

TABLE 20

| Element | Source | Amount (lbs) |
| --- | --- | --- |
| Copper (Co) | Copper Sulfate | 1.500 |
| Iodine (I) | Potassium Iodide | 0.010 |
| Iron (Fe) | Ferrous Sulfate | 25.000 |
| Manganese (Mn) | Manganese Sulfate | 2.500 |
| Selenium (Se) | Sodium Selemite) | 0.025 |
| Zinc (Zn) | Zinc Sulfate | 25.000 |
|  | Carrier | 45.965 |
| Total |  | 100.000 |

Composition of Pig Vitamin Premix

TABLE 21

| Vitamins | Amount |
|---|---|
| Essential | |
| Vitamin A ... (million IU) | 5.0 |
| Vitamin D ... (million IU) | 0.6 |
| Vitamin E ... (thousand IU) | 26.0 |
| Niacin ... (g) | 25.0 |
| d-Pantothenic acid ... (g) | 20.0 |
| Riboflavin ... (g) | 6.0 |
| Vitamin B-12 ... (mg) | 25.0 |
| Optional | |
| Biotin ... (g) | 0.3 |
| Menadione ... (g) | 4.0 |
| Carrier | to 10 lbs |
| Total | 10.0 |

D. 18% Protein Layer Rations for Hens

Table 22

| Ingredients | lbs. | kgs. |
|---|---|---|
| Ground yellow corn | 1242 | 564.5 |
| CLA | 5 | 2.3 |
| Alfalfa meal, 17% | 25 | 11.3 |
| Soybean meal, dehulled | 451.6 | 205.3 |
| Meat and bone meal (47%) | 50 | 23.0 |
| DL-methionine | 1.0 | .5 |
| Dicalcium phosphate | 7 | 3.1 |
| Ground limestone | 174 | 79.1 |
| Iodized salt | 7 | 3.1 |
| Stabilized yellow grease | 37 | 17.2 |
| Mineral and vitamin supplements | | |
| Calcium pantothenate (mg) | 5,000 | |
| Manganese (g) | 52 | |
| Selenium (mg) | 90.8 | |
| Zinc (g) | 16 | |
| Vitamin A (IU) | 6,000,000 | |
| Vitamin D$_3$ (IU) | 2,000,000 | |
| Choline (mg) | 274,000 | |
| Niacin (mg) | 12,000 | |
| Riboflavin (mg) | 2,000 | |
| Vitamin B-12 | 6 | |
| Total | 2000 | 909.4 |

E. Starter and Finisher Rations for Broilers

TABLE 23

| | Starter (up to 24 days) | | Finisher (25 days to market) | |
|---|---|---|---|---|
| Ingredients | lbs. | kgs. | lbs. | kgs. |
| Ground yellow corn | 1,106 | 503 | 1235 | 561 |
| CLA-ester | 5 | 2.3 | 5 | 2.3 |
| Soybean meal, dehulled | 605 | 275 | 420 | 191 |
| Alfalfa meal, 17% | — | — | 25 | 11 |
| Corn gluten meal, 60% | 50 | 23 | 75 | 34 |
| Fish meal, herring, 65% | 50 | 23 | 50 | 23 |
| Meat and bone meal, 47% | 50 | 23 | 50 | 23 |
| Dicalcium phosphate | 10 | 4 | 9 | 4 |
| Ground limestone | 16 | 7 | 14 | 6.3 |
| DL-methionine | 0.8 | 0.3 | — | — |
| Stabilized yellow grease | 101 | 45.7 | 110 | 49.4 |
| Iodized salt | 7 | 3 | 7 | 3 |
| Mineral and vitamin supplement | | | | |
| Calcium pantothenate (mg) | 5,000 | | 5,000 | |
| Manganese (g) | 75 | | 75 | |
| Organic arsenical supplement | 0.1 | | 0.1 | |
| Selenium (mg) | 90.8 | | 90.8 | |
| Zinc (g) | 30 | | 30 | |
| Vitamin A (IU) | 4,000,000 | | 4,000,000 | |
| Vitamin D (IU) | 1,000,000 | | 1,000,000 | |
| Vitamin E (mg) | 2,000 | | 2,000 | |
| Vitamin K (mg) | 2,000 | | 2,000 | |
| Choline (mg) | 503,000 | | 672,000 | |
| Niacin (mg) | 20,000 | | 20,000 | |
| Riboflavin (mg) | 3,000 | | 3,000 | |
| Vitamin B-12 (mg) | 12 | | 12 | |
| Total | 2000.9 | 909.3 | 2000.1 | 909.5 |

F. Grower/Finisher Turkey Rations

TABLE 24

| | Grower (8–16 weeks) | | Finisher (16 weeks-market) | |
|---|---|---|---|---|
| Ingredients | lbs. | kgs. | lbs. | kgs. |
| Ground yellow corn | 1194 | 595 | 1490 | 677.2 |
| Wheat middlings | 50 | 23 | — | — |
| Alfalfa meal, 17% | 25 | 11.3 | 25 | 11.3 |
| Soybean meal, dehulled | 570 | 259 | 335 | 152.3 |
| Meat and bone meal, 47% | 50 | 23 | 50 | 23 |
| Dicalcium phosphate | 32 | 14.5 | 23 | 10.5 |
| Ground limestone | 14 | 6 | 17 | 8 |
| Stabilized yellow grease | 45 | 20.7 | 45 | 20.7 |
| CLA-ester | 5 | 2.3 | 5 | 2.3 |
| Iodized Salt | 10 | 4.5 | 10 | 4.5 |
| Mineral and vitamin supplements | | | | |
| Calcium pantothenate (mg) | 4,500 | | 4,500 | |
| Manganese (g) | 30 | | 30 | |
| Selenium (mg) | 181.6 | | 181.6 | |
| Zinc (g) | 30 | | 30 | |
| Vitamin (IU) | 1,500,000 | | 7,500,000 | |
| Vitamin D (IU) | 1,700,000 | | 1,700,000 | |
| Vitamin E (IU) | 10,000 | | 10,000 | |
| Biotin (mg) | 100 | | 100 | |
| Choline (mg) | 388,000 | | 417,000 | |
| Niacin (mg) | 46,000 | | 48,000 | |
| Riboflavin (mg) | 5,000 | | 5,000 | |
| Vitamin B-12 | 6 | | 6 | |
| Total | 2000 | 909.3 | 2000 | 909.3 |

G. Dry Dog Food Formula

TABLE 25

| Ingredients | Formula 1, % | Formula 2, % |
|---|---|---|
| Meat and bone meal, 50% CP | 8.0 | 15.0 |
| Fish meal, 60% CP, low fat | 5.0 | 3.0 |
| Soybean meal, 44% CP | 12.0 | — |
| Soybean meal, 50% CP | — | 19.0 |
| Wheat germ meal, 25% CP | 8.0 | 5.0 |
| Skimmed milk, dried | 4.0 | 2.75 |
| Cereal grains, mixed | 51.23 | — |

TABLE 25-continued

| Ingredients | Formula 1, % | Formula 2, % |
|---|---|---|
| Corn, flaked | — | 23.25 |
| Wheat bran | 4.0 | — |
| Wheat, flaked | — | 23.35 |
| Animal fat | 1.75 | 2.75 |
| CLA-ester | .25 | .25 |
| Steamed bone meal | 2.0 | — |
| Brewers yeast | 2.0 | 5.0 |
| Fermentation solubles, dehydrated | 1.0 | — |
| Salt and trace minerals | 0.5 | 0.5 |
| Vitamin mixture | 0.25 | 0.25 |
| Ferric oxide | 0.02 | — |
| Total | 100.00 | 100.00 |

H. Semi-Moist Dog Food Formulas

TABLE 26

| Ingredients | Formula 1, % | Formula 2, % |
|---|---|---|
| Soy flakes | 30.9 | 33.5 |
| Meat byproducts, 70% moisture | 32.0 | — |
| Meat and bone meal, dehydrated | — | 7.3 |
| Water | — | 25.6 |
| Sugar | 21.0 | 21.0 |
| Calcium and phosphorous supplement | 3.3 | — |
| Soybean hulls | 3.1 | 3.1 |
| Skimmed milk, dried | 2.5 | — |
| Propylene glycol | 2.1 | 2.1 |
| Sorbitol | 2.0 | 2.0 |
| Animal fat | .75 | 3.95 |
| CLA-ester | .25 | .25 |
| Emulsifiers | 0.9 | — |
| Potassium sorbate | 0.35 | 0.35 |
| Salt | 0.6 | 0.6 |
| Vitamins | 0.25 | 0.25 |
| Total | 100.000 | 100.000 |

What is claimed is:

1. A process for producing low impurity biologically active conjugated linoleic acid comprising providing a linoleic acid containing seed oil, propylene glycol, and an alkali compatible with a nonaqueous medium;

forming a blended reaction mix with said linoleic acid containing seed oil, said propylene glycol, and said alkali compatible with a nonaqueous medium;

isomerizing said linoleic acid containing seed oil by heating to form conjugated linoleic acids; and aquefying to release glycerol;

molecularly distilling said conjugated linoleic acids to form purified conjugated linoleic acids; and treating said purified conjugated linoleic acids with lipase in the presence of glycerol to form triglycerides.

2. The process of claim 1 wherein said heating is carried out at 130 to 165 degrees C. for about 2 to 6.5 hours.

3. A process for producing low impurity biologically active conjugated linoleic acid alkylester comprising providing a linoleic acid containing seed oil, propylene glycol, and an alkali compatible with a nonaqueous medium;

treating said linoleic acid containing seed oil to form alkylesters of said linoleic acid;

forming a blended reaction mix with said alkylesters, said propylene glycol, and said alkali compatible with a nonaqueous medium;

isomerizing said alkylesters by heating to form conjugated linoleic acid alkylesters;

aquefying to release glycerol; and molecularly distilling said conjugated linoleic acid alkylesters to form purified conjugated linoleic acid alkylesters.

4. The process of claim 3 wherein said heating is carried out at 130 to 165 degrees C. for about 2 to 6.5 hours.

5. A process for producing a conjugated linoleic acid alkylester for use in domestic animal feed, food ingredients, or human dietary supplements comprising providing an unrefined linoleic acid alkylester having phosphatidyl residue in the range of about 0.1 to about 0.5 percent;

treating with an alkali alcoholate at low temperature in the presence of a monohydric low molecular weight alcohol to cause isomerization of at least 50 percent of the linoleic acid alkyl ester to conjugated linoleic alkylester at low temperature;

acidifying by addition of an aqueous acid; and molecularly distilling said conjugated linoleic acid alkyl esters to form purified conjugated linoleic acid alkyl esters.

6. The process according to claim 1, wherein the treating step is carried out under a vacuum.

* * * * *